(12) United States Patent
Salazar et al.

(10) Patent No.: US 10,542,195 B2
(45) Date of Patent: Jan. 21, 2020

(54) PRESSURIZED FLUID-SUBMERGED, INTERNAL, CLOSE-RANGE PHOTOGRAMMETRY SYSTEM FOR LABORATORY TESTING

(71) Applicant: BOARD OF TRUSTEES OF THE UNIVERSITY OF ARKANSAS, Little Rock, AR (US)

(72) Inventors: Sean E. Salazar, Fayetteville, AR (US); Richard A. Coffman, Fayetteville, AR (US)

(73) Assignee: Board Of Trustees Of The University Of Arkansas, Fayetteville, AR (US)

( * ) Notice: Subject to any disclaimer, the term of this patent is extended or adjusted under 35 U.S.C. 154(b) by 238 days.

(21) Appl. No.: 15/360,820

(22) Filed: Nov. 23, 2016

(65) Prior Publication Data

US 2017/0150015 A1 May 25, 2017

Related U.S. Application Data

(60) Provisional application No. 62/259,397, filed on Nov. 24, 2015.

(51) Int. Cl.
*H04N 5/225* (2006.01)
*G01F 17/00* (2006.01)
*G01N 33/24* (2006.01)
*G03B 19/16* (2006.01)

(52) U.S. Cl.
CPC .......... *H04N 5/2252* (2013.01); *G01F 17/00* (2013.01); *G01N 33/24* (2013.01); *G03B 19/16* (2013.01)

(58) Field of Classification Search
CPC .......... G01F 17/00; G01N 3/068; G01N 3/12; G01N 33/24; G01N 2203/0069; G01N 2203/0256; G01N 2203/0284; G01N 2203/0647; G03B 19/16; H04N 5/2252; H04N 5/23238; H04N 5/247
See application file for complete search history.

(56) References Cited

U.S. PATENT DOCUMENTS

| 3,457,777 | A | * | 7/1969 | Nielsen | G01N 3/08 73/84 |
| 5,084,764 | A | * | 1/1992 | Day | G01M 3/005 348/84 |
| 6,591,690 | B1 | * | 7/2003 | Crockford | G01N 3/10 73/760 |
| 2004/0076319 | A1 | * | 4/2004 | Fauver | G01N 15/1468 382/133 |
| 2015/0226542 | A1 | * | 8/2015 | Sakashita | G01L 1/24 356/33 |

* cited by examiner

*Primary Examiner* — Huy T Nguyen
(74) *Attorney, Agent, or Firm* — Keith A. Vogt; Keith Vogt Ltd.

(57) ABSTRACT

A device for measuring strain and volume of a soil sample including an enclosure adapted to receive a soil sample within another enclosure. A base adapted to hold the sample enclosure. The device also has a plurality of moveable arms located between the enclosures which may be a spaced distance apart and adapted to move around the sample. Cameras as included on the arms.

14 Claims, 7 Drawing Sheets

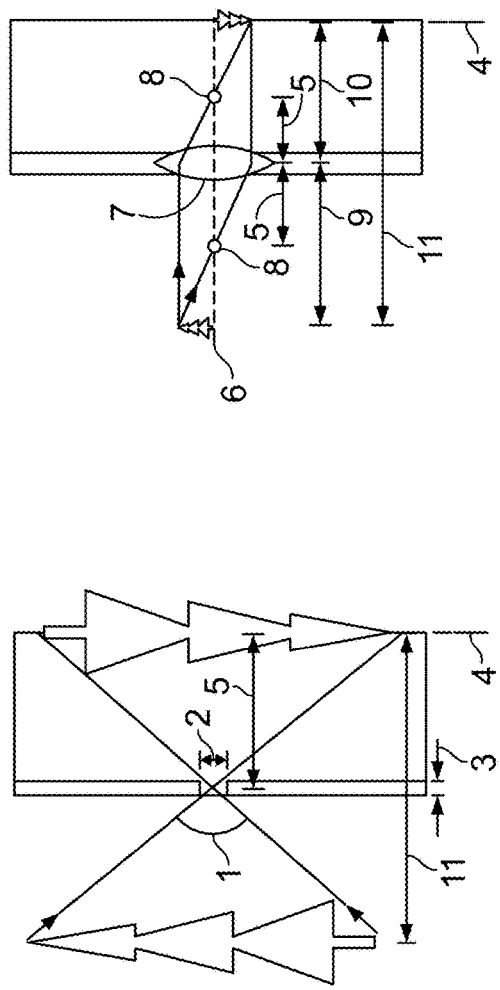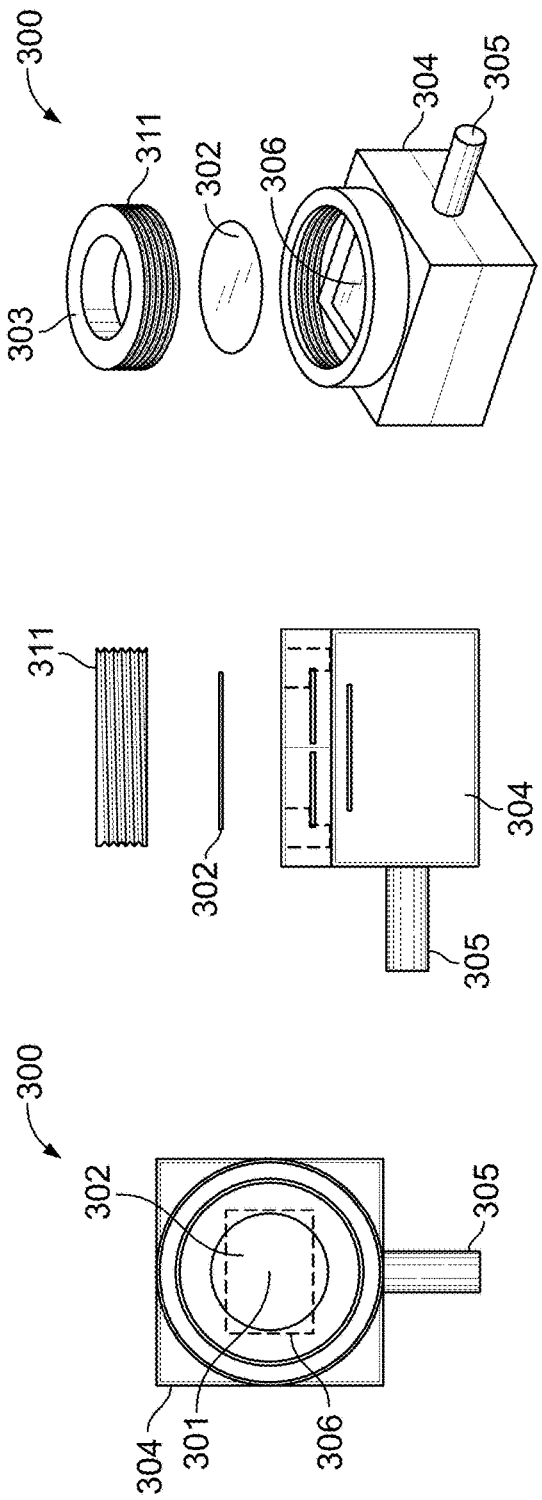

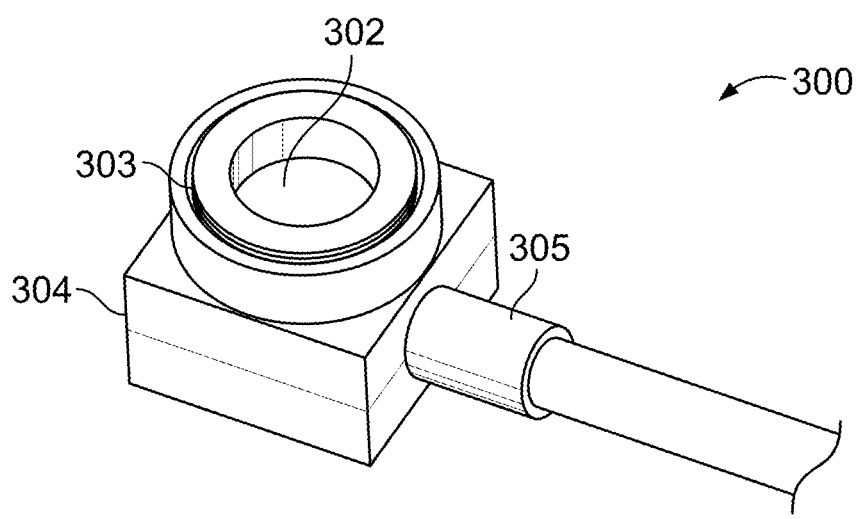
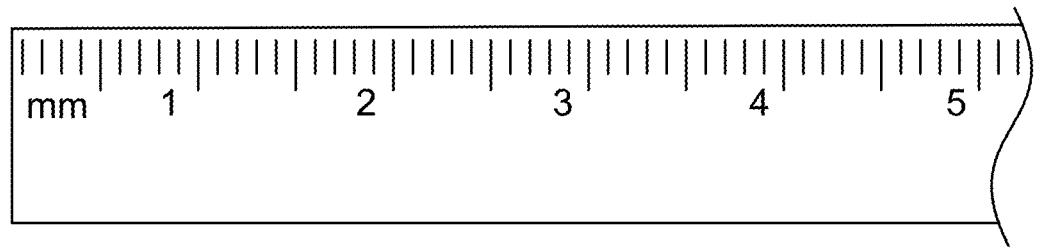
FIG. 4

Pre-consolidation         Post-consolidation

−2.175 mm                    +2.175 mm

PRESSURIZED FLUID-SUBMERGED, INTERNAL, CLOSE-RANGE PHOTOGRAMMETRY SYSTEM FOR LABORATORY TESTING

RELATED APPLICATIONS

Not applicable.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

Historically, when photogrammetric techniques were employed to measure the amount of volume change in specimens being tested in a triaxial device, outside-of-the-cell cameras were utilized. However, light refraction at the 1) confining fluid-cell wall interface and 2) cell wall-atmosphere interface and the curvature of the cell wall have necessitated the use of models to account for the refraction and magnification effects. Furthermore, the cameras surrounding the testing apparatus have been expensive and have required an excessive amount of space to develop the required focal length and lighting conditions. Moreover, the optical elements of the camera equipment have not been addressed in detail, such as optical aberrations, inherent to the camera lenses.

Lenses are typically used to capture and focus light and may be used to increase the field of view. However, errors introduced by refraction of light through lenses, including spherical aberration, coma, field curvature, astigmatism, and barrel, pincushion, and complex distortions are prevalent to varying extents in lenses. Most camera lenses are therefore constructed of multiple lenses (lens array) that are stacked to correct for some aberrations. A careful balance between mitigating one type of aberration and augmenting another type has always existed; therefore it is never truly possible to capture an image that does not contain some type of aberration when a lens or lens array is utilized. Although most cameras use lens arrays, liquid lenses (with variable focus induced by an electrowetting process) have recently been developed for small applications to overcome aberrations encountered with lenses and to adjust the focal length without the need for mechanical servo action; liquid lenses are commonly utilized in many smart phone cameras. The aforementioned focus (inverse of power) of a given lens may be calculated utilizing the Lensmaker's equation (Equation 1) for thin lenses, first developed by English physicist Thomas Young.

$$\frac{1}{f} = \left(\frac{n_1}{n_2} - 1\right)\left(\frac{1}{r_1} - \frac{1}{r_2}\right) \quad \text{(Equation 1)}$$

Where f is the focal length of the lens, $n_1$ is the refractive index of the lens material, $n_2$ is the refractive index of the surrounding medium, $r_1$ is the radius of curvature of the front surface of the lens, and $r_2$ is the radius of curvature of the back surface of the lens.

The pinhole aperture camera is the most basic type of camera and is often overlooked in favor of a lensed camera. However, despite, and perhaps because of its simplicity, the pinhole camera may provide: 1) images free of the optical distortions that are inherent to the use of lenses, 2) images with virtually infinite depth of field, 3) wide viewing angles, and 4) a foundation for understanding the basic concepts involved in the field of optics, specifically related to the use of cameras. The primary advantage of using a lens, as opposed to a simple pinhole, is that a lens can capture and focus more light, without requiring long exposure times, thereby increasing optical resolution (defined as the ability to resolve detail). When resolution is not the most critical objective of a camera application, a simple pinhole aperture camera may provide a viable alternative to a typical lensed camera. Pinholes have been used for centuries for purposes of viewing and tracing images onto drawings prior to utilizing photo-sensitive materials for photography purposes. Moreover, the basic concepts of pinhole optics were instrumental to the formulation of the theory of light. The theory was supported by the earliest written observations of multiple phenomena related to light, specifically diffraction, interference, and polarization of light, through pinholes.

The design of a pinhole aperture is relatively simple; however, certain considerations are necessary to optimize image quality. Unlike lensed cameras, pinhole cameras rely on diffraction, not refraction. The theory and equations for pinhole apertures were suggested by early researchers. Attempts have also been made to refine the relationship between the optical phenomena in more recent years. However, the theoretical limits should only be used as a guideline, because the optimal pinhole aperture diameter is often better determined experimentally. The optimal pinhole diameter is limited by resolution (larger diameters correspond with poorer resolution), by Fresnel (near-field) and Fraunhofer (far-field) diffraction limits, and by the ability to gather light (smaller diameters correspond with higher diffraction interference and allow less light to be collected). The optimal pinhole diameter for optical applications often relates to the "Airy disk" which is the bright, focused spot, central to a diffraction pattern through a perfectly circular aperture.

To be able to withstand high pressures, a camera is typically sealed in pressure-resistant or, more commonly, pressure-compensating housings. These housings are typically bulky, expensive, and do not allow for direct optical observation because light must first pass through a transparent thermoplastic barrier (i.e. acrylic plastic) before reaching the camera. To combat this, fluids such as silicone oil or mineral oil may be used in electronics applications where exposure to the fluid is unavoidable or desired. The direct contact between the electronics and fluid will not cause short-circuiting, due to the inert and non-ionic properties of the oil. Furthermore, even at high pressures, the silicone oil does not crush the components of the camera even though the components are directly subjected to the fluid. This direct immersion allows for pressure resistant design, without the need for a housing; thereby also allowing for direct optical observation.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIG. 2A provides a real image formation illustrated by a ray diagram for the diffraction of light through a pinhole aperture.

FIG. 2B provides a real image formation illustrated by a ray diagram for the refraction of light through a lens.

FIG. 3A is a schematic of a front view of an embodiment of the present invention.

FIG. 3B is a schematic of an exploded side view of an embodiment of the present invention.

FIG. 3C is a schematic of an exploded orthogonal view of an embodiment of the present invention.

FIG. 4 illustrates a board camera with pinhole aperture ("BCPA") for an embodiment of the present invention.

BRIEF SUMMARY OF THE INVENTION

Figures 1A, 1B:
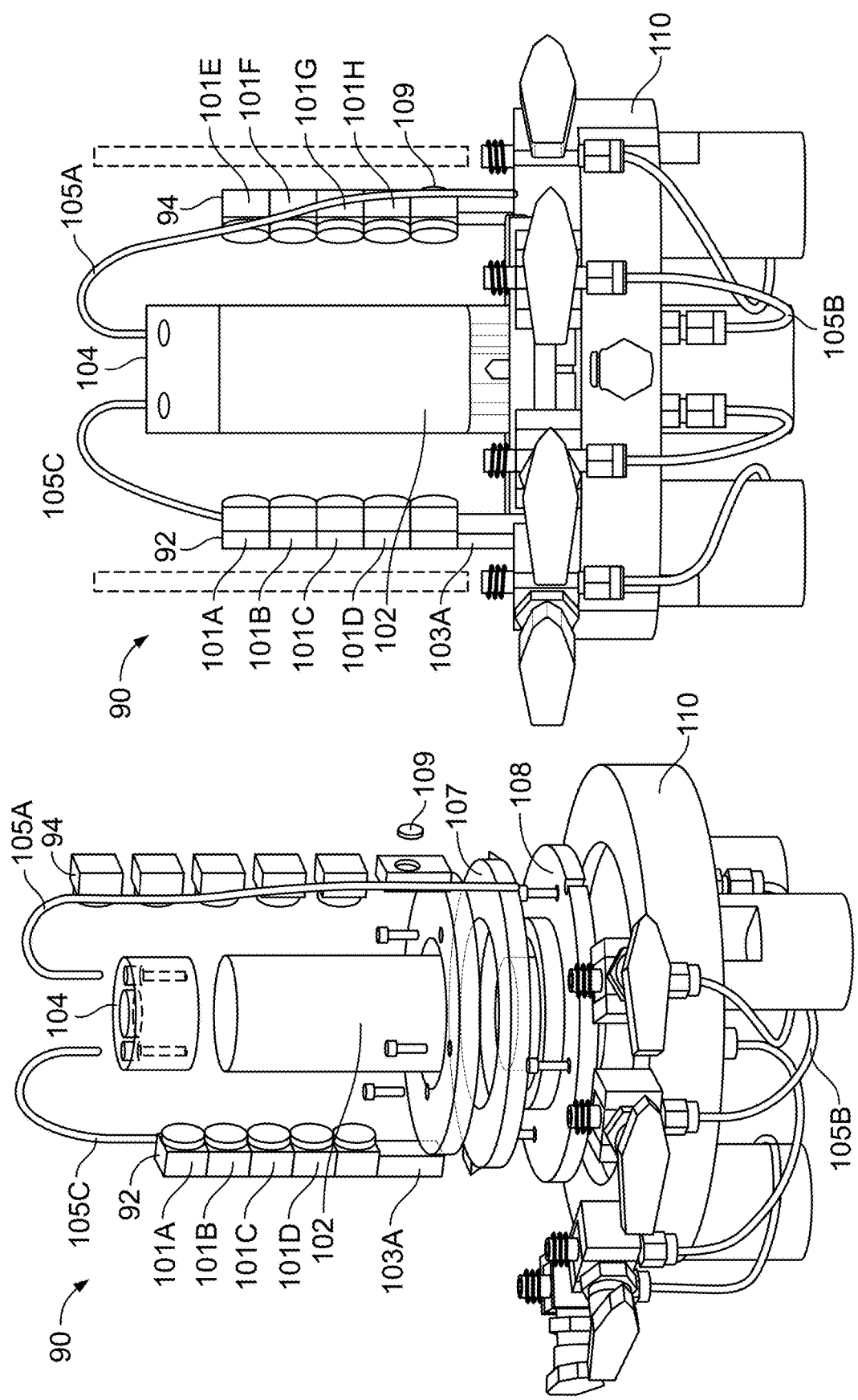
FIGS. 1A, 1B and 1C are schematics of guided camera track system mounted on a triaxial apparatus base for an embodiment of the present invention.

In one embodiment, the present invention provides a system that allows for 1) unobstructed, remote monitoring of a specimen, such as a soil specimen, within the apparatus during all stages of testing, 2) the capture of digital images and videos of the specimen during all stages of testing, and 3) the performance of three-dimensional modeling of the specimen at any given stage of testing using the principles of photogrammetry.

In another embodiment, the present invention provides a system that has been developed for direct integration into a triaxial testing apparatus, which is a commonly used geotechnical laboratory testing device.

In another embodiment, the present inventions provides a system that provides solutions to the need for alternative methods to monitor specimens during testing.

In another embodiment, the present invention provides a system that utilizes small board cameras located within the triaxial cell, that overcome pressure and space constraints.

In another embodiment, the present invention provides optical designs for board cameras that provide high quality images within a confined space, even when the camera is immersed in a confining fluid.

In another embodiment, the present invention provides a small open body board camera with a pinhole aperture (BCPA).

In another embodiment, the present invention provides a system that is configured to meet the physical space requirements of placing multiple cameras within a standard triaxial cell.

In another embodiment, the present invention provides a system that is configured to enable direct contact between electronic components of the camera and the confining fluid.

In another embodiment, the present invention provides a system that is configured to meet the space requirements for developing the appropriate focal length.

In another embodiment, the present invention provides a system that is configured to meet the need for operation in high cell pressures during use.

In another embodiment, the present invention provides a system that is configured to, during testing, to provide sufficient coverage of the entire specimen area with minimal camera deployment.

In another embodiment, the present invention provides a system that provides accurate measurements of specimen dimensions, cross-sectional area, level of strain, volume, and failure plane angle, as a function of time. These parameters are critical to 1) constitutive modeling and 2) prediction of specimen behavior.

In another embodiment, the present invention provides a system that enables an unobstructed image of the specimen during imaging.

It is to be understood that both the foregoing general description and the following detailed description are exemplary and explanatory only and are not restrictive of the invention, as claimed.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1C:
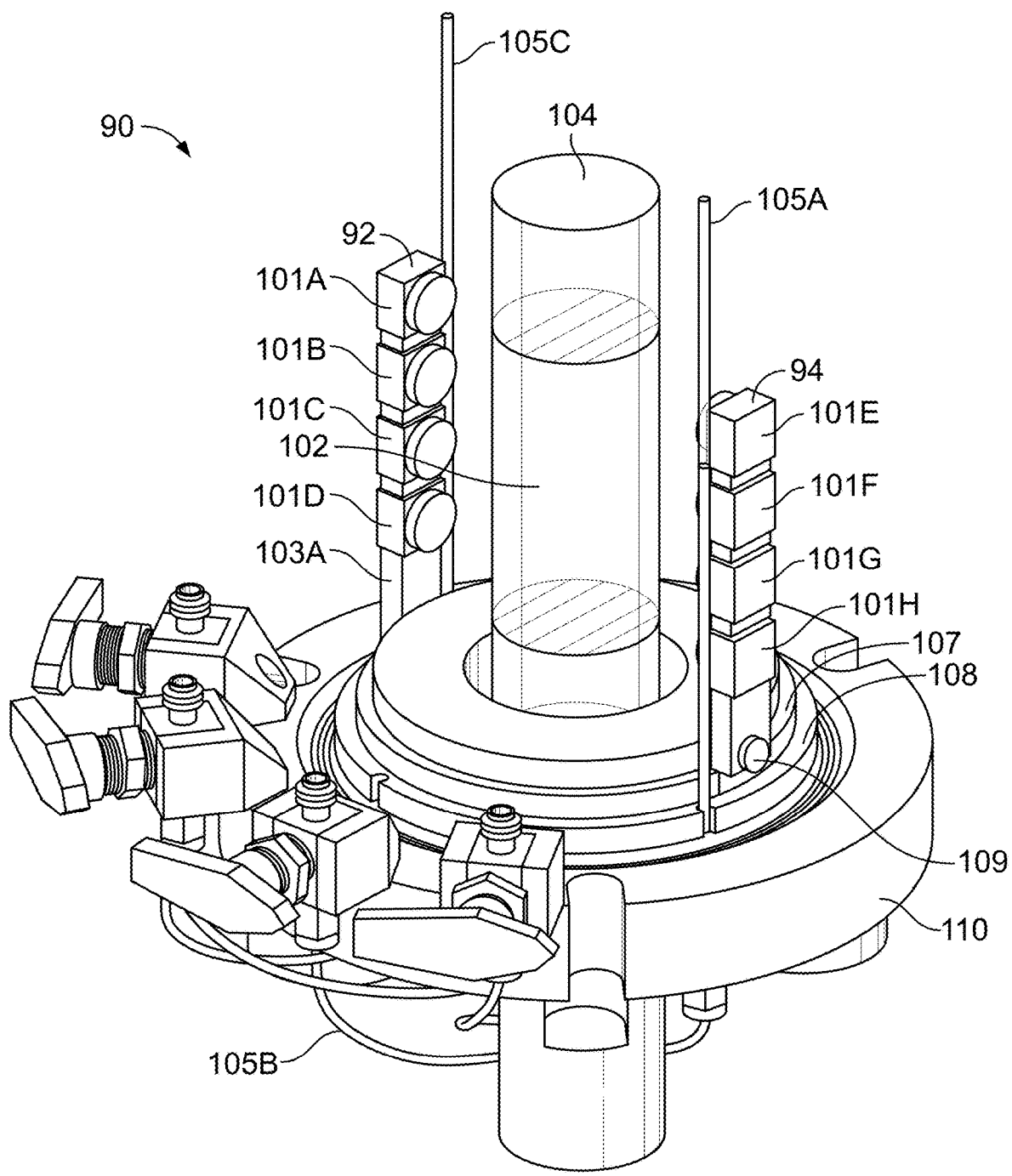

As shown in FIG. 1, in one embodiment, the present invention provides an imaging system 90 configured for analyzing a sample, such as a soil sample 102, that may be located in transparent container 104. Container 104 may include drain lines 105A-105C and is, in turn, located in a sealed container known as a triaxial cell (not shown).

In one embodiment, the design of the optical and mechanical components of system 90 are arranged to monitor triaxial specimen 102 from within a triaxial cell, while submerged in confining fluid, and subjected to high pressures. To meet these requirements, system 90 includes a plurality cameras that are also arranged to 1) minimize space requirements, 2) provide each camera with the necessary focal length, depth of field, and field of view, 3) permit full submersion within a pressurized confining fluid, and 4) provide complete specimen coverage around the entire circumference and vertical height of a sample.

In a preferred embodiment, the present invention uses a plurality of cameras since it was not possible to observe the entirety of the specimen with a single camera. Specifically, the field of view of an individual camera (21 mm [0.83 in.]) was smaller than the height of the specimen (7.62 cm [3.0 in.]). Therefore, in a preferred embodiment, multiple cameras are provided as was discussed above. By using multiple cameras, individual areas of the specimen were monitored and the photographs of the individual areas may be stitched together using post-processing software. To achieve this, in preferred embodiment, the cameras used are board camera pinhole aperture ("BCPA") cameras. As shown in FIG. 1, opposingly located one or more arrays, such as array 92 and array 94, may consist of a plurality of BCPAs. In a preferred embodiment, array 92 has BCPAs 101A-101D and array 94 has BCPAs 101E-101H. The BCPAs may be mounted to towers 103A and 103B that are adapted to rotated around specimen 102. To provide rotational movement, the towers may be mounter to track 107 that rotates within base 108 inside of the cell. In another embodiment, track 107 may be designed to rotate using pairs of small magnets; one magnet may be mounted to the track and the other magnet may be located at various positions outside of triaxial cell wall such as along base 108. The rotational movement allows for the BCPAs to capture still frames at prescribed intervals during the rotation.

A challenge overcome by the embodiments of the present invention is the need to provide an imaging system that may fit within the small size of the triaxial cell (11.43 cm [4.5 in.] inside diameter Trautwein Soil Testing Equipment Co. triaxial cell). Only 3.81 cm [1.5 in.] of space surrounded the 3.81 cm [1.5 in.] diameter specimen. To overcome this challenge, in one aspect, the present invention provides small closed circuit board cameras (with dimensions of 14 mm [0.55 in.] by 14 mm [0.55 in.] by 13 mm [0.51 in.]) that may be placed into the cell in between the cell wall and the soil specimen. A preferred DCPA for use in the triaxial cell is a 8.38 mm [0.33 in.] format SONY CCD sensor, capable of obtaining 700 LoHR, and 976 horizontal by 582 vertical effective pixels.

In other embodiments, a camera and lens combination may be used as well instead of the DCPA arrangement. For this embodiment, given the space constraints within the triaxial cell, the design needs a very small lenses (on the order of 2.0 mm in diameter) with unusually high refractive indices (greater than 1.8) to give the appropriate focal length when immersed in the silicone oil.

To avoid damage to the sensitive electronics of the cameras, while still ensuring saturation of the specimen (by utilizing pressurized fluid instead of pressurized air to prevent gas diffusion across the membrane), silicone fluid (PSF-5 cSt, Trautwein Soil Testing Equipment Co.) may be used to confine the specimens and surrounded the cameras. Properties of the silicone fluid include: low viscosity (5 cSt), specific gravity of 0.918, dielectric constant of 2.60, dielectric strength of 375, and index of refraction of 1.397. Due to the high refractive index of the oil (relative to air), standard lenses were unable to focus when immersed in the oil. Specifically, the index of refraction of the silicone oil (1.397) was much greater than the index of refraction of air (1.000 in a perfect vacuum). Although unknown, it was estimated that the index of refraction of the lens material was between 1.48 and 1.60 (for crown or flint glass). The increase in the index of refraction from 1.000 to 1.397 reduced the difference in the indices of refraction between the two media (air-glass and oil-glass) and thereby increased the required focal length.

As discussed previously, limited space is available to deploy the cameras. This space constraint limits the maximum achievable focal length, the distance between the object and the lens, as shown in the ray diagram shown in FIGS. 2A and 2B. The minimum focal length values, for the standard lenses that were included with purchase of the board cameras when tested in air, were between 4 cm and 6 cm [1.6 in. and 2.4 in.]. These distances corresponded to images with the highest sharpness; therefore, focused images could not be obtained when using cameras with the standard lenses within the available confined space of 3.81 cm [1.5 in.].

The Lensmaker's equation (previously presented as Equation 1) was employed to determine the optical properties of a lens that would enable collection of images when immersed in silicone oil. However, given the immersion medium, lens, or lens array, with a correct refractive index greater than 1.8 is needed to provide the appropriate focal length (approximately 24 mm [0.94 in.]) within the physical space limitations (3.81 cm [1.5 in.]).

To withstand the cell pressures during testing (up to 1,034 kPa [150 psi]), the conventional cameras were flooded behind the aperture, filling all of the air space with oil. It was observed, in original testing of the lensed cameras, that the focal length of the lens arrays permanently changed after being subjected to typical pressures. This was attributed to the compression of the small void spaces between the lenses when subjected to pressure resulting in permanent deformation of the lenses, thereby altering the optical properties of the lens array.

To overcome the limitations of focal length, refractive properties of the confining fluid, cell pressure, and specimen coverage, a lens less pinhole aperture board camera may be used with the present invention. A preferred camera 300 is shown in FIGS. 3A-3C and FIG. 4. Camera 300 includes pinhole aperture 301, pinhole substrate 302, threaded barrel 303, aperture box 304, video signal and power supply cable 305 and CCD sensor 306. In a preferred embodiment, an 8.38 mm [0.33 in.] format board camera encased in aperture box 304 with a M12×0.5 threaded opening 310; 2) threaded barrel 303, with external threads 311, may be used for seating and adjusting pinhole aperture substrate 302; and 3) a laser cut pinhole aperture 301 (75 µm opening), centered at a specified focal length (2.0 mm) from the camera sensor 306. The design of BPCA 300 enables images to be collected from inside of the triaxial cell while the cameras were immersed in silicone oil and subjected to high pressures. For this embodiment of the present invention, a preferred aperture diameter may be approximated, based on Equation 2.

$$f = 2r^2/\lambda \qquad \text{(Equation 2)}$$

Where f is the focal length, r is the radius of the pinhole opening (or aperture), and $\lambda$ is the design wavelength.

However, unlike for a lens, the f variable used in Equation 2 was associated with the distance between pinhole aperture 301 and the camera sensor plane, as previously depicted in FIG. 2B. Furthermore, as discussed previously, unlike lensed cameras, pinhole cameras have infinite depth of field, therefore this type of aperture allowed for the entire image to be in focus.

To obtain sharp images, and to maximize resolution, the edges of the pinhole need to be precisely cut and the diameter of the pinhole must be small. Additionally, the thickness of the substrate must be thin to allow for the widest viewing angle (as shown previously in FIG. 2B). Therefore, various pinhole sizes 75, 100, and 150 microns [2.95×10⁻³, 3.94×10⁻³, and 5.91×10⁻³ in.] were laser cut into the center of a 9.5 mm [0.375 in.] diameter wafer substrate (National Aperture, Part Number 1-75+B-2, 1-100+B-2, and 1-150+B-2), respectively. The steel substrate (300 series stainless steel) had a thickness of 12.7 microns [$5\times10^{-4}$ in.] and both sides were blackened (+B-2) to absorb any stray light within the aperture box.

The design optical wavelength (415 nm) was selected based on the results obtained from a relative light intensity test that was conducted by examining a diffuse reflectance fluoropolymer reference material (Spectralon, Labsphere, Inc.) using a spectroradiometer (ASD FieldSpec Pro Hand-Held 2 portable spectroradiometer). Although a peak value of 580 nm was observed, a reduced value of 415 nm was utilized because of the refractive index ratio (1.397) that was associated with silicone oil being used as the confining fluid instead of air. Furthermore, this wavelength (415 nm) was selected because the final position of the pinhole aperture was fine-tuned (in relation to the camera image plane) using threaded barrel 303 that screwed into the aperture box 306.

A recess may be placed into the threaded barrel to enable the wafer substrate to be mounted to the barrel. The aforementioned three aperture diameters were tested at various distances from the camera sensor, and it was found that the 75 micron [$3.94\times10^{-3}$ in.] diameter aperture provided the best image quality when the substrate was located 2.0 mm away from the image plane, as assessed by visual inspection of the acquired images.

The video cables of the cameras are connected to a wire harness that connects to a nine-pin feed-through connector located within the top cap of the triaxial device. The feed-through allowed for electrical signals to travel into and out of the triaxial device. The video wires that were connected to the cameras were also connected to the pins on the nine-pin feed-through connector; the opposite side of the pins were also connected the input channels of an eight-way video/audio switch (Maituo MT-VIKI 8 Port VGA Switch). The single video output channel from the video/audio switch was then connected to a Universal Serial Bus 2.0 Digital Video Adapter (Sabrent USB-AVCPT). Each camera was supplied with external power (DC 12V) from a common external power supply (Enercell 3-12 VDC 1A AC Adapter) that provided power to all of the cameras simultaneously via the nine-pin feed-through connector. The video feed from each of the cameras was subsequently received and displayed by switching the video/audio switch. The software that was included with the video adapter (Sabrent USB 2.0 Video Capture Creator with Audio) was utilized to capture still frames from the video feed that was obtained from each of the cameras. In other embodiments, the power, grounding, and video signals from each of the BCPA devices may be all controlled with a small Raspberry Pi computer and relay switch board, both contained within the triaxial cell.

Figure 5A:
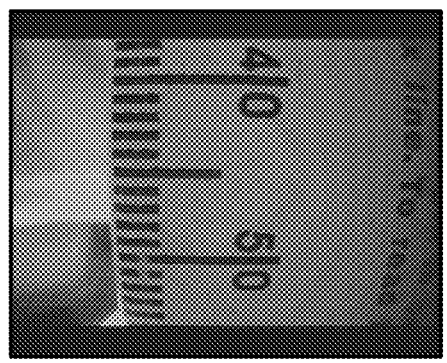
FIG. 5A is a still frame of an object in air for one embodiment of the present invention.
Figure 5B:
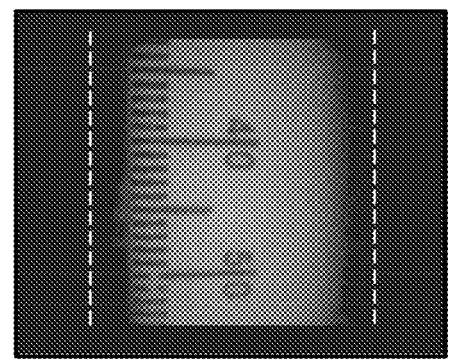
FIG. 5B is a still frame of an object in oil for the embodiment of FIG. 5A.

Still frames, captured from the video feed of a board camera with a lens (located in air and immersed within PSF-5 cSt silicone oil), are presented in FIGS. 5A and 5B, respectively. Still frames, captured with the BCPA (located in air and immersed within PSF-5 cSt silicone oil), are presented in FIGS. 5C and 5D, respectively. An example of linear distortion in images captured using a lens is evident in FIG. 5A and the inability of the camera to collect focused light through the lens to form a real image is displayed in FIG. 5B. As explained previously, because the lens was designed to work in air, the index of refraction of the silicone oil prevented the camera that was fully immersed within oil from obtaining a focused image.

Figure 5C:
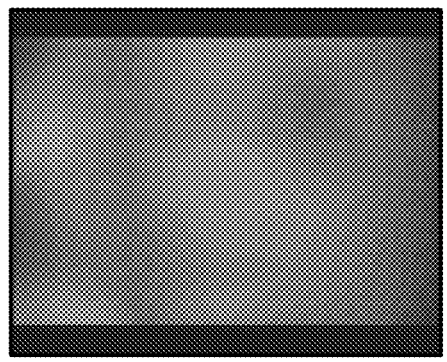
FIG. 5C is a still frame of an object in air for another embodiment of the present invention.
Figure 5D:
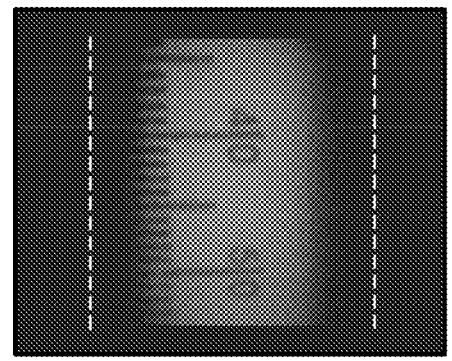
FIG. 5D there should is a still frame of an object in oil for the embodiment of FIG. 5D.

It was determined that the captured light on the far left and far right edges of the images collected using the BCPA faded abruptly and completely (as indicated by the areas to the left and right of the dashed white lines in FIGS. 5C and 5D). This phenomenon was attributed to a combination of physical and optical influences. The aperture barrel material blocked the edges of the CCD sensor along the longer (horizontal) side of the CCD sensor (due to the proximity of the barrel to the sensor). Thereby, light was prevented from reaching the edges of the CCD sensor that led to the black appearance. Although not required, the proximity limitation may be overcome, by enlarging the inside diameter of the threaded barrel. However, it was determined that the dimensions of the shorter (vertical) side of the sensor provided sufficient coverage of the object (if the camera was rotated in such a way that the camera cable exited from the camera in the horizontal plane as shown previously) and therefore an increase in the inside diameter of the barrel was not necessary. Furthermore, the "Airy disk" was covered the entire camera sensor so no visible diffraction patterns were present.

The comparison between images captured with a lens and those captured with a pinhole aperture show there is a significant difference in the amount of light exposure. The lens (FIGS. 5A and 5B) allowed for maximum light gathering. The pinhole aperture (FIGS. 5C and 5D) allowed for minimal light entry, due to the small size of the opening (75 micron [$3.94\times10^{-3}$ in.] diameter). In typical pinhole photography, this minimal amount of light entry is commonly overcome with longer exposure times; however, for the type of board camera that was used, it was not possible to control the exact exposure time (electronic shutter time varied between 1/60 and 1/100,000 seconds, as per the camera manufacturer). Furthermore, the board camera switched into "night mode" (monochromatic light gathering) when the illuminance levels dropped below a certain threshold (0.1 lux). Chromatic aberration may have been present in the captured images but it was not possible to detect this type of aberration due to the monochromatic nature of the images. Although the lighting was not modified to collect the images presented in FIGS. 5A-5D, higher quality imagery of the soil sample may be obtained by providing lighting that surrounds the sample. In a preferred embodiment, the present invention provides surrounding lighting by utilizing one or more dome lights. In a preferred embodiment two 17.8 cm [7 in.] diameter dome light sources are arranged to surround the entire triaxial chamber to enhance the imagery.

With aid of the guided camera track system, multiple still frames may be captured with the individual BCPAs along the length of the soil specimen, at prescribed intervals during rotation around the circumference of the specimen. Because of the overlapping fields of view of adjacent BCPAs, in the vertical direction and in circumferential direction, common points were acquired within captured images, and the individual geopositions of the cameras were calculated, allowing for post-process stitching of the collected images. PhotoModeler (Eos Systems, Inc. 2014) was utilized to calculate the photogrammetric properties of the BCPA. These properties included the focal length, format size (physical dimensions of the sensor) and principal point (intersection between principal axis and image sensor). PhotoModeler was also used to determine the geoposition of each of the individual BCPAs. Specifically, the positions of the BCPAs were determined by using unique, pre-selected targets that were adhered to a 1.5 in. [38 mm] diameter by 3 in. [76 mm] tall brass specimen and that were automatically recognized within the software. The PhotoModeler obtained photogrammetric properties and geopositions corresponded well with manual (caliper) measurements.

Using repeatable rotation intervals, and therefore known geopositions of each of the individual BCPAs, PhotoModeler was used to match common points within the captured images that thus enabled generation of a dense point cloud for any object that was viewed by the BCPAs. This point cloud was then meshed to calculate the dimensions and volume of the viewed object. By utilizing this method (PhotoModeler), the volume of the brass specimen that was obtained was 91.92 cm$^3$. The volume obtained using manual (caliper, pi tape) measurements was 91.93 cm$^3$, resulting in an estimated error of 0.01 percent.

In other embodiments, the present invention provides multiple BCPA devices that may be employed to enable photographic coverage of the entire surface of the specimen (during consolidation and shearing up to 15 percent axial strain in triaxial compression or triaxial extension). Given the vertical viewing angle of each of the individual BCPAs (approximately 73 degrees), the BCPA devices may be stacked to allow for overlapping fields of view along the length of the specimen in the axial direction. To minimize the required number of BCPAs, a rotating platform may be used to allow for several overlapping images at each point around the specimen in the radial direction. Due to the presence of two diametrically opposed vertical drain lines, within the triaxial cell that enable drainage from the top of the specimen through the top platen, a full 360 degree revolution of a single BCPA tower was not possible. Therefore, at least two diametrically opposed BCPA towers may be used and the towers are configured to rotate between the two drain lines. Each tower may be rotated with 155 degrees of rotation. Given the horizontal fields of view of the individual BCPA devices and the required image overlap for photogrammetric processing, the towers are rotated around the specimen and the towers were stopped at a desired degree interval to acquire images.

To facilitate smooth and precise rotation of the two BCPA towers around the soil specimen, the rotating platform may be configured to utilized a stiff, low-friction, thermoplastic material (Polyoxymethylene [Delrin]), and an L-shaped slot design. A 25.4 mm×25.4 mm×12.7 mm [1 in.×1 in.×0.5 in.] neodymium magnet (52 MGOe) located on the outside of the cell is circumferentially rotated around the outside of the cell wall to pull a 6.35 mm [0.25 in.] diameter neodymium magnet, that was mounted to the base of one of the BCPA towers, causing the towers to rotate circumferentially around the vertical axis.

Figure 6:
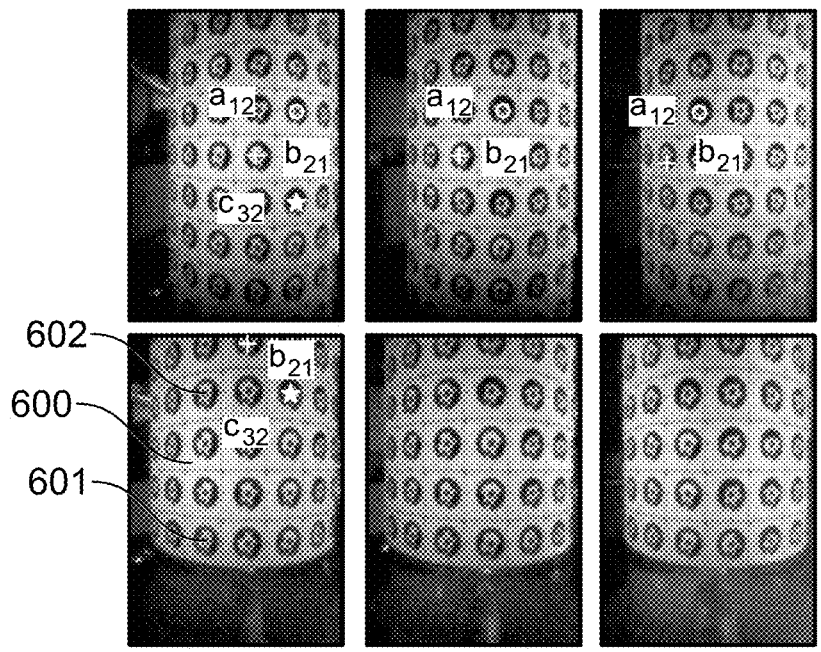
FIG. 6 provides vertically and horizontally overlapping photographs captured with an embodiment of the present invention.

In other embodiments, the present invention provides methods that may be utilized to calibrate and validate the camera monitoring system and to reconstruct a digital three-dimensional model of a sample. An exemplary sample used with the methods of the present invention was a brass test specimen with known dimensions (3.81 cm [1.5 in.] diameter by 7.62 cm [3.0 in.] length). Each BCPA device is calibrated by capturing a series of images of a printed PhotoModeler calibration grid. The images of the calibration grid are subsequently analyzed using the PhotoModeler Scanner software (Eos Systems, Inc. 2015) to obtain the necessary intrinsic camera parameters (focal length, sensor format size, and principal point). As shown in FIG. 6, brass specimen 600 may have thereon PhotoModeler coded targets (ringed automatically detected [RAD]), such as 601 and 602. The targets may be adhered to the side of the aforementioned brass specimen and the specimen is placed on a flat surface where additional RAD targets are adhered to the surface on which the specimen rested (96 targets total). A previously calibrated digital single lens reflex (DSLR) camera (Canon 5D Mark II with fixed 28 mm Nikkor lens) with known properties (aperture controlled, f/13, ISO 1250, 28 mm fixed lens, and as calibrated using a PhotoModeler calibration grid) was used to capture images of all sides of the specimen. Each RAD target was captured in a minimum of four images. The DSLR-acquired images were processed using the PhotoModeler Scanner software and the center of each target was precisely surveyed to within 0.2 mm [0.0079 in.]. The same brass specimen, with the same adhered targets, was then placed within the triaxial cell and the target covered surface was captured using the BCPA devices that were mounted on at least two spaced-apart towers. Five degree intervals were utilized to acquire a total of 320 images. As shown in FIG. 6, adjacent images were overlapped in both the axial and radial directions. The common control points within the DSLR and the BCPA images (ex. $a_{12}$, $b_{21}$, $c_{32}$ in FIG. 6) were used to photogrammetrically derive the location and orientation of each of the individual BCPA devices, at a given rotation interval, within the cell.

To determine the practical range of rotation intervals (number of stations during rotation), specific sets of the captured images were removed from the total 320 images (as captured from the 5-degree rotation interval). Specifically, the locations and orientations of BCPA devices were derived by using different intervals (45, 30, 15, and 5-degree rotation intervals). Three-dimensional recreations, from PhotoModeler Scanner software, of the calibration specimen surface (control points) and BCPA device locations and orientations, within the triaxial cell, are presented in FIG. 6. Photographic measurements obtained from the software, based on the DSLR survey, were utilized to calculate a volume for the brass test specimen. A volume of 91.58 cm$^3$ was obtained, which corresponded to an estimated difference of 0.34 percent when compared to the volume calculations that were obtained from manual measurements (caliper and pi tape). Given repeatable positioning of the BCPA towers at a desired rotation interval, the derived location and orientation values for the individual BCPA devices are able to be used, in conjunction with PhotoModeler software, to measure points on the surface at any axial strain level, for any soil specimen that was tested within the triaxial cell. The measured points resulted in a point cloud that was then used to identify the surfaces of the given specimen. The point cloud was then exported from PhotoModeler Scanner and imported into AutoCAD Civil 3D software (Autodesk, Inc. 2015) to obtain accurate three-dimensional reconstructions of any specimen.

In yet other embodiments, the present invention provides one or more small board cameras with a pinhole aperture designed for deployment inside of a triaxial cell to enable measurement of the axial and volume of soil specimens. The camera components may be fully immersed in oil and may be located very close to the soil specimen. To resist the high pressures that are commonly encountered within the triaxial cell during triaxial testing (up to 1,034 kPa [150 psi]), silicone oil allowed to enter behind the camera face and to surround the CCD sensor. The relatively high refractive index of silicone oil (as compared to the refractive index of air) influenced the light entering into the traditional lenses or lens arrays yielding severely out-of-focus images (because the refractive index of the lens or lens array closely matched the refractive index of the lens confining fluid). Thus, the present invention provides, in certain embodiments, a careful balance between resolution, light entry, and field of view. To optimize the design of the camera, one or more BCPA cameras may be provided which have an infinite depth of field (including very close depths) and a lack of any of the optical aberrations associated with lenses. Other advantages of using a pinhole-type camera are as follows; the BPCA: 1) is not adversely affected by the refractive properties of the immersion fluid (silicone oil); 2) requires very little space to develop appropriate focal length and require less space than a lens or lens array; 3) may be designed to provide very large viewing angles without the need for a lens, and 4) can withstand pressure. By utilizing a BCPA, images may be obtained within a triaxial cell.

In yet other embodiments, the present invention provides a photogrammetry system that utilizes a plurality of board cameras modified with custom, lens barrel-mounted pinhole apertures, which has an adjustable length, to adjust the field of view of the camera by changing the distance between the pin hole and sensor.

In other embodiments, the pinhole attached to barrel is adapted to move in toward and/or away from the sensor to increase or decrease the field of view. The camera devices, with a preferred number being 10, are mounted to at least two diametrically-opposed camera towers (five on each tower) and the camera towers are mounted to a rotating track within the testing apparatus. The number of cameras (ten total) and the rotating track allow for full photographic coverage of the soil specimen. The individual modified board cameras may be remotely controlled by the user through electronic connections.

The internal photogrammetry system (with all associated electronics) is fully submerged within the pressurized confining fluid (nonionic, silicone oil) that surrounds the specimen and is able to withstand pressures of up to 150 pounds per square inch (equivalent to approximately 350 feet of water depth). By placing the optical components internally within the testing apparatus (as opposed to outside of the apparatus), the user may view the specimen directly, without obstruction from the 1) apparatus acrylic confining cell, 2) confining fluid contained within the cell, and 3) the metal confining rings and tie rods. Besides circumventing physical obstructions, internal placement also eliminates the need to mathematically correct for the refraction of light through multiple media (confining fluid, cell wall, and air outside of the apparatus). These corrections are complex and are prone to error.

Digital images and videos that are captured with the system during testing may be processed with commercially-available photogrammetry software to accurately reconstruct three-dimensional models of the specimen.

In other embodiments, the present invention further includes software that allows the user to switch between camera and video feeds. The software also acquires imagery from the feeds by communicating with the circuit board. In addition, the present invention further uses a mechanized rotating track for the camera towers.

The results from the evaluation of the internal cell photogrammetry techniques using the embodiments of the present invention are discussed below. As shown in Table 1, the differences of the various volume measurement techniques relative to the reference (water displacement technique) fell within one-half of one percent.

TABLE 1

Comparison of small-acrylic analog specimen volumes as obtained using five different techniques.

| Volume Determination Method | Volume of Specimen [$cm^3$] Repetition | | | Mean [$cm^3$] | Difference from Reference [%] |
|---|---|---|---|---|---|
| | 1 | 2 | 3 | | |
| Water Displacement | 94.97 | 95.60 | 95.47 | 95.35 | Reference |
| Manual Measurements | 95.82 | 95.82 | 95.82 | 95.82 | 0.50 |
| 3-D Scan | 95.64 | — | — | 95.64 | 0.31 |
| DSLR Photogrammetry | 95.62 | — | — | 95.62 | 0.29 |
| Internal Photogrammetry | 95.22 | — | — | 95.22 | −0.13 |

The accuracy of the embodiments of the present invention exceeded what would have been expected based on values reported in the literature even for the relatively small size of the specimens that were utilized for evaluation (nominal dimensions of 7.62-cm length and 3.81-cm diameter), as compared to larger size specimens contained within the literature (typically, 10.16-cm length and 5.08-cm diameter, or 14.22-cm length and 7.11-cm diameter).

Although it appeared that derived camera location difference was sensitive to the photograph interval (degree of separation between sets of photographs), as indicated by convergence of camera locations, the effect was considered negligible (within 0.045 pixels for the maximum difference in camera location). The relationship between derived camera location and photograph interval was not directly meaningful. Therefore, the influence of the photograph interval on the determination of specimen volume was examined (Table 2).

TABLE 2

Comparison of large-acrylic analog specimen volumes as determined during internal photograph interval sensitivity test.

| Rotation Interval [Degrees] | Number of Photos | Computational Cost [minutes] | Specimen Volume $V_T$, [$cm^3$] | Summary Statistics | |
|---|---|---|---|---|---|
| 45 | 40 | 120 | 135.17 | Mean Volume [$cm^3$] | 135.56 |
| 30 | 60 | 180 | 135.37 | Standard Deviation [$cm^3$] | 0.34 |
| 15 | 110 | 330 | 135.87 | Standard Error [$cm^3$] | 0.17 |
| 5 | 320 | 960 | 135.80 | Coefficient of Variation [%] | 0.25 |
| | | | | Range [$cm^3$] | 0.70 |

Note:
Photographs acquired using internal board cameras.

For the volume (as calculated from four photogrammetric reconstructions, using 45-, 30-, 15-, and five-degree photograph intervals), the standard deviation was equal to 0.34 cm3, and the range was equal to 0.70 cm3. The determination of volume was therefore not sensitive to the photograph interval. Thus, to 1) match the 20-degree gaps surrounding the drain tubes within the triaxial cell, thereby providing consistent photograph intervals, and 2) maintain a sufficient level of photogrammetric redundancy by providing increased overlap between photographs, an interval of 20 degrees may be used with the embodiments of the present invention. This resulted in 80 photographs and approximately 240 minutes of processing time per photogrammetry project.

4.3 Testing of Internal Photogrammetry System on Soil Specimens

The volume of the soil specimens was determined at various levels of axial strain during both the CTC and RTE tests, as well as during the UC test. The CTC and RTE tests were performed in an undrained condition and therefore the total volume of the specimen was not expected to change during the shearing phase of each test. Likewise, the UC test was undrained. The volumes that were measured during each test, and the summary statistics for each test, support this conclusion. The results from the CTC test are presented in Table 3.

TABLE 3

Volumes of kaolinite soil specimen as determined throughout the triaxial compression test and corresponding summary statistics.

| Testing Phase | Axial Strain $\varepsilon_a$, [%] | Volume $V_T$, [cm$^3$] | Summary Statistics | |
|---|---|---|---|---|
| Consolidation | Pre-consolidation | 89.72 | Change in Volume During Consolidation [cm$^3$] | 6.56 |
| | 0 | 83.16 | | |
| Shear | 2 | 82.92 | Mean Volume During Shear [cm$^3$] | 83.37 |
| | 4 | 83.28 | | |
| | 6 | 83.27 | Standard Deviation [cm$^3$] | 0.37 |
| | 8 | 83.28 | Standard Error [cm$^3$] | 0.14 |
| | 11.5 | 84.10 | Coefficient of Variation [%] | 0.45 |
| | 15 | 83.55 | Range [cm$^3$] | 1.18 |

Note:
Photographs acquired using internal board cameras.

The volume change during the consolidation phase was determined to be 6.56 cm3, using the internal photogrammetry techniques of the present invention. As a comparison, the volume change determined from the pore pump was equal to 6.81 cm3 (temperature corrected) and the change calculated from the displacement transducer was equal to 6.70 cm3 (using the assumption that the cross-sectional area of the specimen remained constant during K0 consolidation). The internal photogrammetry approach therefore underpredicted the volume change by 3.7 percent, as compared to the pump measurements, and by 2.1 percent, as compared to calculations using the change in specimen height.

The results from the RTE test and the UC test are presented in Table 4 and Table 5, respectively.

TABLE 4

Volumes of kaolinite soil specimen as determined throughout the triaxial extension test and corresponding summary statistics.

| Testing Phase | Axial Strain $\varepsilon_a$, [%] | Volume $V_T$, [cm$^3$] | Summary Statistics | |
|---|---|---|---|---|
| Shear | 0 | 79.88 | Mean Volume During Shear [cm$^3$] | 80.30 |
| | 8 | 80.40 | | |
| | 10 | 80.32 | Standard Deviation [cm$^3$] | 0.27 |
| | 12 | 80.28 | Standard Error [cm$^3$] | 0.12 |
| | 15 | 80.64 | Coefficient of Variation [%] | 0.34 |
| | | | Range [cm$^3$] | 0.76 |

Note:
Photographs acquired using internal board cameras.

TABLE 5

Volumes of kaolinite soil specimen as determined throughout the unconfined compression test and corresponding summary statistics.

| Testing Phase | Axial Strain $\varepsilon_a$, [%] | Volume $V_T$, [cm$^3$] | Summary Statistics | |
|---|---|---|---|---|
| Shear | 0 | 91.01 | Mean Volume During Shear [cm$^3$] | 91.35 |
| | 2 | 91.46 | | |
| | 4 | 90.99 | Standard Deviation [cm$^3$] | 0.69 |
| | 6 | 90.90 | Standard Error [cm$^3$] | 0.26 |
| | 8 | 90.75 | Coefficient of Variation [%] | 0.75 |
| | 11.5 | 91.57 | Range [cm$^3$] | 2.00 |
| | 15 | 92.75 | | |

Note:
Photographs acquired using DSLR camera.

For the CTC, RTE, and UC tests, the small changes in total volume, during undrained shearing, were likely a result of the sensitivity to limited refinement of the 3D model surface (function of the number of targets on the membrane). As indicated by the standard deviation of total volumes calculated during the CTC test (0.37 cm3), as compared to the standard deviation during the RTE test (0.27 cm3), the variability was greater for the CTC test. The likely cause of the greater variability during the CTC test was that the target refinement was more sensitive to the local deformations on the surface of the specimen during compression (uneven bulging) than during extension (fairly uniform necking). Comparison with the results from the UC test (standard deviation of 0.69 cm3) revealed that even with the high resolution DSLR camera photogrammetry technique there was variability in the volumes, further supporting that the model refinement (number and density of targets on surface of the specimen) affected the accurate determination of specimen volume throughout a test.

Figure 7:
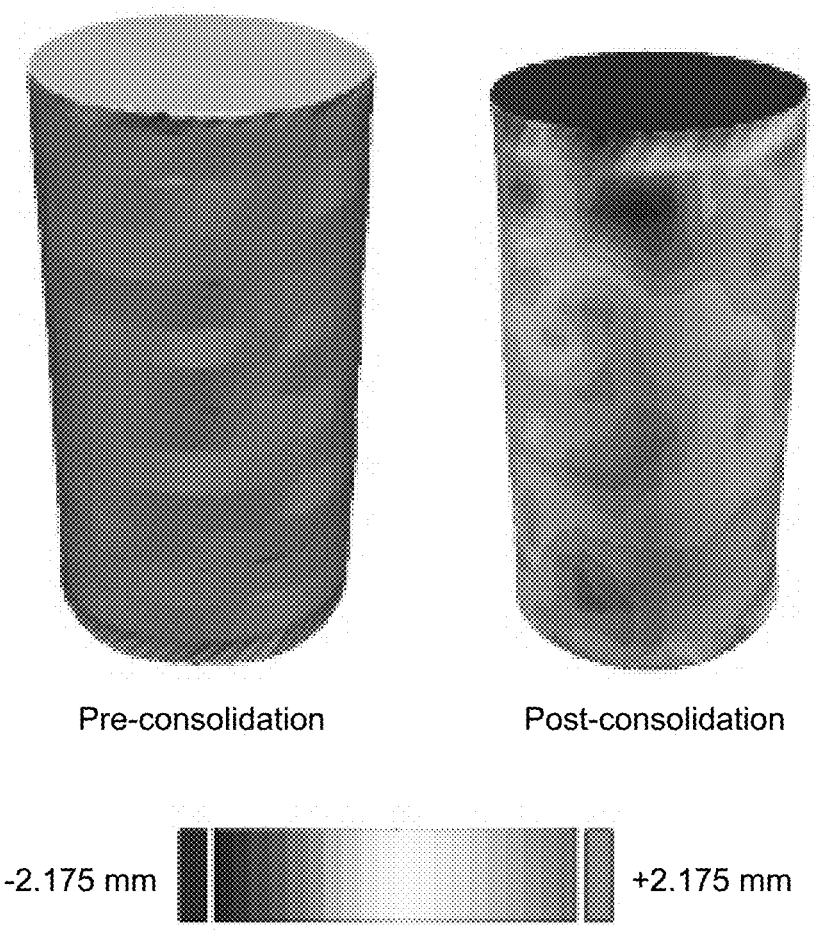
FIG. 7 provides a visualization of photogrammetry-obtained, three-dimensional models of a kaolinite specimen during K0-consolidation phase of triaxial test.
Figure 8A:
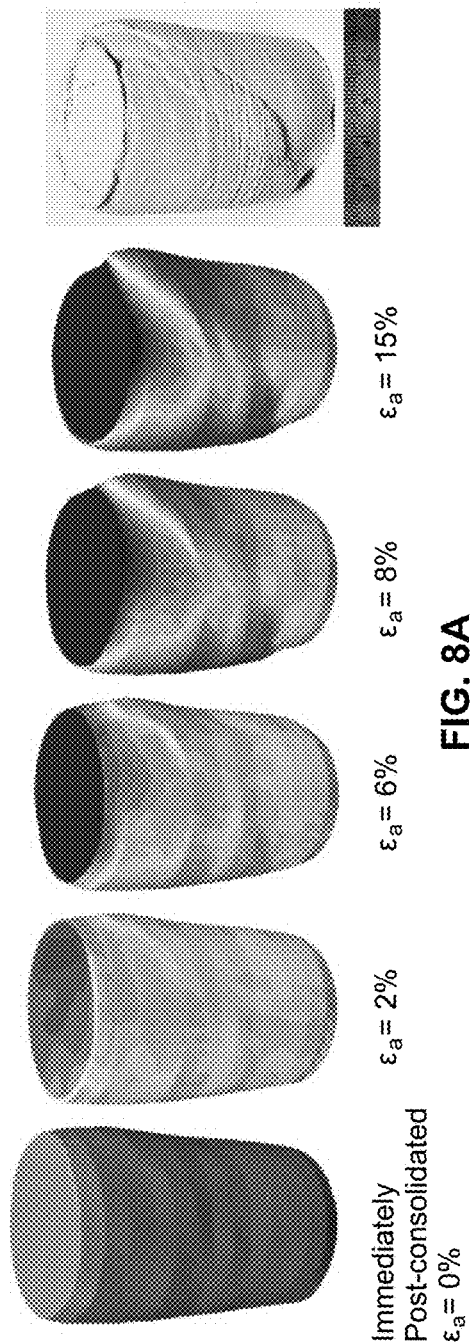
FIG. 8A provides a visualization of photogrammetry-obtained, three-dimensional models of a kaolinite test specimen during for a conventional triaxial compression.
Figure 8B:
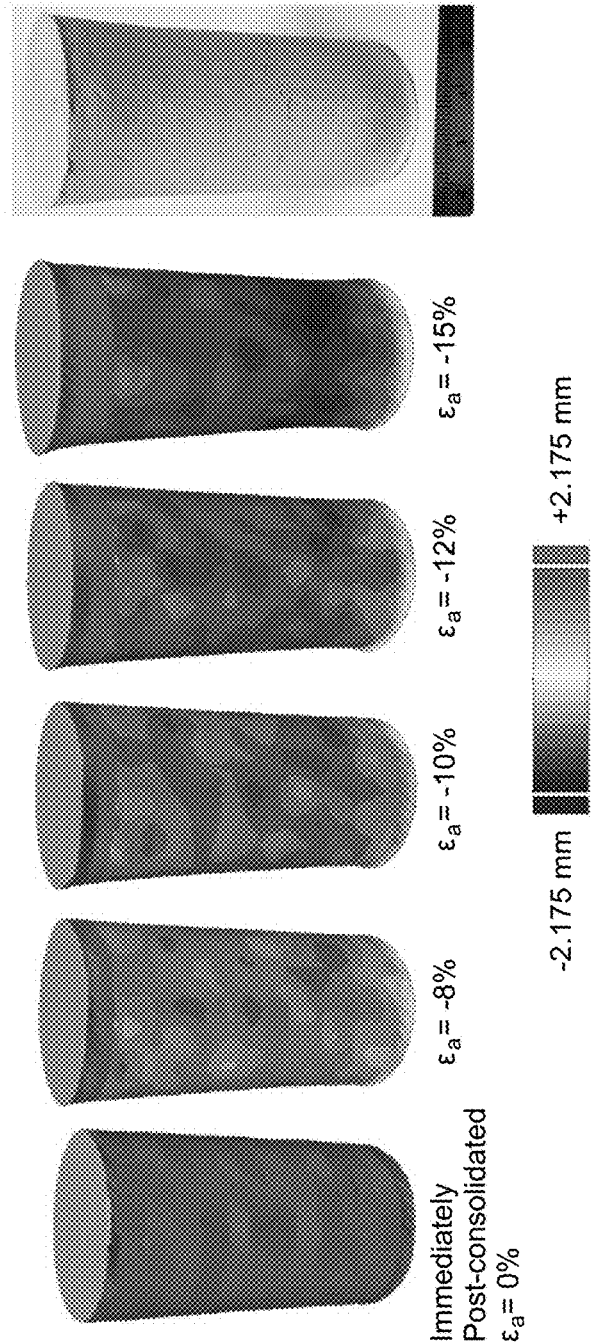
FIG. 8B provides a visualization of photogrammetry-obtained, three-dimensional models of a kaolinite test specimen during for a conventional triaxial compression.

The localized displacements of each specimen were visualized qualitatively for the CTC and RTE tests. Specifically, the displacements were visualized for the consolidation phase of testing, as presented in FIG. 7, and for the shearing phase, as presented in FIGS. 9A and 9B. During the consolidation phase, the small strains in the radial direction of the specimen were somewhat unexpected, as the triaxial testing apparatus was programmed for K0-consolidation by which the diameter of the specimen should have remained constant throughout the consolidation phase of the test. In the CTC test (FIG. 9A), the actual failure plane of the soil specimen was evident from the shear banding behavior at larger strains (greater than eight percent axial strain). Conversely, necking behavior was observed for the specimen in the RTE test (FIG. 9B).

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A device to determine the radial and axial strain of a specimen comprising: a plurality of small board pinhole cameras, located within a triaxial cell; and said pinhole cameras are mounted on diametrically-opposed arms and said arms are mounted to a rotating track.

2. A device for measuring strain and volume of a soil sample comprising:
  a first enclosure adapted to receive a soil sample, said first enclosure located within a second enclosure;
  a base adapted to hold said first enclosure;
  a plurality of moveable arms located between said enclosures, said arms located a spaced distance apart and adapted to move around said all or some of said first enclosure; and
  said arms including one or more cameras.

3. The device of claim 2 wherein said plurality of said cameras are small board cameras.

4. The device of claim 2 wherein each camera includes at least one charge-coupled device (CCD) sensor used in conjunction with at least one precision pinhole aperture to capture images of the sample.

5. The device of claim 4 wherein the cameras are fully immersed in electronics-grade silicone oil and are able to withstand cell pressures up to 1,034 kPa [150 psi].

6. The device of claim 2 wherein the cameras are pinhole cameras.

7. The device of claim 2 wherein each of said arms include at least 4 cameras and said are diametrically-opposed.

8. The device of claim 7 wherein said cameras are arranged to provide full photographic coverage of the specimen.

9. The device of claim 8 wherein said cameras are fully submerged within the pressurized confining fluid.

10. The device of claim 7 wherein said cameras are stacked to allow for overlapping fields of view along the length of the specimen in the axial direction.

11. A method for measuring strain and volume of a soil sample comprising the steps of:
  providing a first enclosure adapted to receive a soil sample, said first enclosure located within a second enclosure;
  providing a base adapted to hold said first enclosure;
  providing a plurality of moveable arms located between said enclosures, said arms located a spaced distance apart and include one or more camera cameras;
  rotating said arms around said sample while said cameras capture images of said sample; and
  analyzing said images to determine the strain and volume of said sample.

12. The method of claim 11 wherein said cameras are arranged to provide full photographic coverage of the specimen while only rotating partially around said sample.

13. The method of claim 11 further providing the step of fully submerging said cameras within a pressurized confining fluid.

14. The method of claim 11 wherein said cameras are stacked to allow for overlapping fields of view along the length of the specimen in the axial direction as said cameras are rotated.

* * * * *